(12) United States Patent
Castellane et al.

(10) Patent No.: US 6,859,764 B2
(45) Date of Patent: Feb. 22, 2005

(54) DETECTING, CLASSIFYING AND LOCALIZING MINOR AMOUNTS OF AN ELEMENT WITHIN A SAMPLE OF MATERIAL

(75) Inventors: Raymond M. Castellane, Vicksburg, MS (US); Falih H. Ahmad, Cornelius, NC (US); Bartley P. Durst, Clinton, MS (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/406,159

(22) Filed: Apr. 3, 2003

(65) Prior Publication Data

US 2003/0171899 A1 Sep. 11, 2003

(51) Int. Cl.⁷ ................................................ G06F 11/32
(52) U.S. Cl. ....................................... 702/189; 356/303
(58) Field of Search ........................... 702/189, 19, 20, 702/22, 23, 27, 28, 30, 147; 356/32, 35.5, 36, 300, 303

(56) References Cited

U.S. PATENT DOCUMENTS

| | | | |
|---|---|---|---|
| 5,526,299 A | | 6/1996 | Coifman et al. |
| 6,316,782 B1 | * | 11/2001 | Akselrod et al. ........... 250/582 |
| 6,411,914 B1 | | 6/2002 | Mack |
| 6,675,106 B1 | * | 1/2004 | Keenan et al. ................ 702/28 |
| 6,687,620 B1 | * | 2/2004 | Haaland et al. ............... 702/22 |

OTHER PUBLICATIONS

Ahmad, F.H. etal., A Wavelet Packets Technique for the Detection of Anomalies in Fourier Transform Infrared Interferograms, Spectroscopy Letters, 35(4), 527–541 (2002), Marcel Dekker, Inc.

* cited by examiner

Primary Examiner—Hal Wachsman
Assistant Examiner—Edward Raymond
(74) Attorney, Agent, or Firm—Earl H. Bougiter

(57) ABSTRACT

Minute amounts of material, such as a contaminant, are detected, identified and located using a single procedure that eliminates the need for using complex and sometimes redundant instrumentation setups, multiple (and sometimes overlapping) analytic processes, or both. In a preferred embodiment, a series of processing steps enables one to detect, identify, and localize minute amounts of particular elements, e.g., contaminants, in material being tested. Data sets, suitable for characterizing components of samples at least spectrally and spatially, are collected from at least one uncontaminated sample of material (the "baseline" or "control") and a sample of material under test (MUT) that may contain contaminants. Comparison of these data sets, using the procedures of the present invention, enables ready identification of minute amounts of material in any sample. The use of existing conventional procedures may require that multiple sets of data be taken or multiple processes be applied.

6 Claims, 10 Drawing Sheets

Interferogram of a Non-Contaminated Sample

Interferogram of Material Under Test (MUT)- Contaminated

DETECTING, CLASSIFYING AND LOCALIZING MINOR AMOUNTS OF AN ELEMENT WITHIN A SAMPLE OF MATERIAL

STATEMENT OF GOVERNMENT INTEREST

The invention described herein may be manufactured and used by or for the Government of the United States of America for governmental purposes without the payment of any royalties thereon or therefor.

FIELD OF INVENTION

Provided is an analytic tool used in non-destructive spectral analysis to identify electromagnetic properties that indicate the presence of minor amounts of an element, such as a contaminant.

BACKGROUND

Details about electromagnetic properties of material are needed to establish those material characteristics suited to particular purposes such as camouflage, concealment and deception. One way of obtaining these details is to energize material with select forms of electromagnetic energy and observe the results using spectral analysis.

Several well known data handling techniques are used for spectral analysis in the optical portion of the electromagnetic spectrum including: Classical Least Squares, Partial Least Squares, Beer's Approximation and Principal Component Regression. *Infrared Quantitative Analysis,* Nicolet Instrument Corporation, Madison, Wis. 1997. Straightforward use of any of these techniques requires optimization of instrumentation for the particular technique. One may wish to apply two or more of the techniques to the same data. The optimum instrumentation configuration may vary with the desired result, e.g., to obtain the optimum signal-to-noise ratio (SNR). This often leads to a unique, yet expensive and labor-intensive, solution, e.g., taking the same data with different instrumentation configurations or settings.

It is known that signals can be encoded and decoded efficiently to reduce the amount of data handled, such as number of bits, bandwidth, or storage, while retaining salient characteristics of the decoded signal. Examples include audio and video bandwidth compression schemes. Jack, Keith, *Video Demystified: a Handbook for the Digital Engineer,* High Text Interactive, Inc., San Diego, Calif., 1996.

A characteristic frequency response is often used to analyze materials, as is coupling thereto an associated temporal or spatial interval, or both. Such analyses may be done using a windowed Fourier Transform such that different sized windows correspond to the scale of the desired transient feature. This method correlates the signal to all windowed exponentials and checks for significant correlations. Because measurements may not be independent, information thus obtained may be redundant.

One method of reducing computation costs while maintaining accuracy is described in U.S. Pat. No. 5,526,299, Method and Apparatus for Encoding and Decoding Using Wavelet-Packets, to Coifman et al., Jun. 11, 1996, incorporated herein by reference. This method uses a library of modulated wavelet packets (combinations of dilations and translations) to extract features by correlating this library with a signal of interest while maintaining orthogonality of the set of waveforms thus selected.

Wavelets are mathematical functions that separate data into different frequency components, allowing each component to be analyzed with a resolution matched to the component's scale. They have advantages over traditional Fourier methods in analyzing physical situations where the signal contains discontinuities and sharp spikes, such as with spectral data collected using an interferometer.

Wavelet algorithms process data at different scales or resolutions, e.g., a signal viewed from a large "data window" exhibits but gross features, whereas a signal viewed from a small data window allows detailed features to be seen. Wavelet analysis enables use of approximating functions with non-zero mean values in finite domains and zero mean value elsewhere.

The wavelet analysis procedure adopts a wavelet prototype function, termed an "analyzing wavelet" or "mother wavelet." Temporal analysis (translation) is performed with a contracted, high frequency version of the mother wavelet, while frequency analysis (dilation) is performed with a dilated, low frequency version of the same wavelet. The combination of dilation and contraction, or translation, is done in what is termed a wavelet packet. Wavelets are zero mean value orthogonal basis functions that are non-zero within a defined space and time. They are used to transform an operator by applying to the operator a finite number of scales (dilations) and positions (translations), yielding transform coefficients to populate a matrix. Feature extraction is enabled by correlating a library of waveforms, or waveforms taken from a known source, with the signal of interest, while maintaining orthogonality of the selected set of waveforms.

Because the original signal or function can be represented in terms of a wavelet expansion (using coefficients in a linear combination of the wavelet functions), data operations can be performed using just the corresponding wavelet coefficients. Further, by choosing the best wavelets adapted to your data as in a "best tree" approach, or truncating the coefficients below a threshold, data may be sparsely represented. This sparse coding makes wavelets an excellent tool in the field of data compression or when economy of computational resources is desired.

Generically speaking, wavelets are produced by constructing a basis function, shifting it by some amount, and changing its scale. Then that structure is applied in approximating a signal. The procedure is repeated by again taking the basic structure, shifting it, and scaling it. Applying this to the same signal yields a new approximation. This procedure is repeated until a desired result is achieved. An inherent advantage of this "scaled analysis" is its relative insensitivity to noise because it measures the average fluctuations of the signal at different, yet appropriate, scales.

A basic wavelet is the Haar wavelet, a property of which is "compact support," meaning that it vanishes outside of a finite interval. Haar wavelets are not continuously differentiable which somewhat limits their applications.

A basis function may be explained by reference to digital analysis and vectors. Every two-dimensional vector (x,y) is a combination of the vector (1,0) and (0,1). These two vectors are the basis vectors for (x,y) since x multiplied by (1,0) is the vector (x, 0), and y multiplied by (0,1) is the vector (0,y). The sum is (x,y). These basis vectors have the inherent valuable property of orthogonality.

These concepts may be related to basis functions. Instead of the vector (x,y), we have a function f(x). Imagine that f(x) is a spectral response, say the frequency A of a particular material's response. A may be constructed by adding sines and cosines using combinations of amplitudes and frequencies. The sines and cosines are the basis functions in this example (and also the elements of Fourier synthesis). An additional requirement may be imposed in that these sines and cosines be orthogonal. This is accomplished by choosing the appropriate combination of sine and cosine terms whose inner products add to zero. Thus, the particular set of functions that are orthogonal and that construct f(x) constitute appropriate orthogonal basis functions.

Windowing can be understood by what is done to reduce the number of calculations and increase the accuracy in Fourier transforms. If J(t) is a non-periodic signal, the summation of the periodic functions, sine and cosine, does not accurately represent the signal. The signal may be artificially extended to make it periodic, but this would require additional continuity at the endpoints. The windowed Fourier transform (WFT) is one solution to representing a non-periodic signal. The WFT separates an input signal f(t) into sections. Each section is analyzed for its frequency content separately. If the signal has sharp transitions, the input data is "windowed" so that the sections converge to zero at the endpoints. This windowing is accomplished via a weight function that places less emphasis near the interval's endpoints than in the middle. The effect of the window is to localize the signal in time.

To approximate a function by samples, and to approximate the Fourier integral by the discrete Fourier transform, requires applying a matrix whose order is the number of sample points, n. Since multiplying an n×n matrix by a vector requires on the order of $n^2$ arithmetic operations, the problem worsens as the number of sample points increases. However, if the samples are uniformly spaced, then the Fourier matrix may be factored into a product of just a few sparse matrices. The resulting factors may be applied to a vector in a total of order n log n arithmetic operations, i.e., the Fast Fourier Transform (FFT). By analogy to FFT, wavelets may be packaged as "packets" and analysis continue in a manner similar to the FFT while taking advantage of the unique capabilities of wavelet analysis.

A basis function varies in scale by "dissecting" the same function or data space using different scale sizes. For example, a signal in the domain from 0 to 1 may be represented using two step functions from 0 to ½ and $1/_2$ to 1. The original signal may be divided again using four step functions from 0 to ¼, ¼ to ½, ½ to ¾, and ¾ to 1. And so on, each set of representations coding the original signal with a particular resolution or scale. There are other similarities between Fourier and wavelet transforms.

The fast Fourier transform (FFT) and the discrete wavelet transform (DWT) are both linear operations that generate a data structure that contains $\log_2$ n segments of various lengths, usually filling and transforming the data structure into a different data vector of length $2^n$. The mathematical properties of the matrices involved in the transforms are similar as well. The inverse transform matrix for both the FFT and the DWT is the transpose of the original. As a result, both transforms can be viewed as a rotation in function space to a different domain. For the FFT, this new domain contains basis functions that are sines and cosines. For the wavelet transform, this new domain contains more complicated basis functions called wavelets, mother wavelets, or analyzing wavelets.

Both transforms have another similarity. The basis functions are localized in frequency, making mathematical tools such as power spectra (how much power is contained in a frequency interval) and "scalegrams" useful at picking out frequencies and calculating power distributions.

A scalegram of a time series is the average of the squares of the wavelet coefficients at a given scale. Plotted as a function of scale, it depicts much of the same information as does the Fourier power spectrum plotted as a function of frequency. Implementing the scalegram involves summing the product of the data with a wavelet function, while implementing the Fourier power spectrum involves summing the data with a sine or cosine function. The formulation of the scalegram makes it a more convenient tool than the Fourier transform because certain relationships between the different time scales become easier to see and correct, such as seeing and correcting for photon noise.

There are basic dissimilarities between Fourier and wavelet transforms that lead to a fuller understanding of the benefits of using wavelet packets in a preferred embodiment of the present invention.

A basic dissimilarity is that individual wavelet functions are localized in space. Fourier sine and cosine functions are not. This localization feature, along with a wavelets' localization of frequency, makes many functions and operators using wavelets "sparse" when transformed into the wavelet domain. This sparseness, in turn, results in a number of useful applications such as data compression, practical detection of features in images, and noise removal from a time series.

One way to see the time-frequency resolution differences between the Fourier transform and the wavelet transform is to look at the basis function coverage of the time-frequency plane. FIG. 1 shows a windowed Fourier transform, where the window is simply a square wave. It shows Fourier basis functions, time-frequency tiles, and coverage within the time-frequency plane. The square wave window truncates the sine or cosine function to fit a window of a particular width. Because a single window is used for all frequencies in the WFT, the resolution of the analysis is the same at all locations in the time-frequency plane.

An advantage of wavelet transforms is that the windows vary. To isolate signal discontinuities, very short basis functions are desirable. Conversely, to obtain detailed frequency analysis, some very long basis functions are desirable. A way to achieve this is to have short high-frequency basis functions and long low-frequency ones, exactly what wavelet transforms provide. FIG. 2 shows the coverage in the time-frequency plane with one wavelet function (Daubechies wavelet basis functions), time-frequency tiles, and coverage within the time-frequency plane.

Note that wavelet transforms do not have a single set of basis functions like the Fourier transform that utilizes just the sine and cosine functions. Instead, wavelet transforms have an infinite set of possible basis functions. Thus wavelet analysis provides immediate access to information that can be obscured by other time-frequency methods such as Fourier analysis. Wavelet transforms comprise an infinite set. The different wavelet families make trade-offs between how compactly the basis functions are localized in space and how smooth they are. Within each family of wavelets (such as the Daubechies family) are wavelet subclasses distinguished by the number of coefficients and by the level of iteration. Wavelets are classified within a family most often by the number of vanishing moments. This is an extra set of mathematical relationships for the coefficients that must be satisfied, and is directly related to the number of coefficients. For example, within the Coiflet wavelet family are Coiflets with two vanishing moments and Coiflets with three vanishing moments. FIG. 3 illustrates several different wavelet families.

Dilations and translations of the mother wavelet, or analyzing wavelet, Φ (x), define an orthogonal basis, or wavelet basis:

$$\Phi_{(s,l)}(x) = 2^{\frac{-s}{2}} \Phi(2^{-s}x - l) \quad (1)$$

The variables s and l are integers that scale and dilate, respectively, the mother function Φ(x) to generate wavelets, such as a Daubechies wavelet family. The scale index, s, indicates the wavelet's width, and the location index, l, gives its position. Notice that the mother wavelet functions are re-scaled, or "dilated" by powers of two ($2^{\pm s}$), and "translated" by integers (l). Once the mother wavelet functions are known, everything is known about the basis.

To span the data domain at different resolutions, the analyzing (mother) wavelet is used in a scaling equation:

$$W(x) = \sum_{k=1}^{n-2} (-1)^k C_{k+1} \Phi(2x + k) \quad (2)$$

where W(x) is the scaling function for the mother function Φ(x), and $C_k$ represents the wavelet coefficients. The wavelet coefficients satisfy linear and quadratic constraints of the form $$\sum_{k=0}^{N-1} C_k = 2, \sum_{k=0}^{N-1} C_k C_{k+2l} = 2\delta_{l,0} \quad (3)$$

where δ is the delta function and l is the location index.

One of the most useful features of wavelets is the ease with which one may choose the defining coefficients for a given wavelet system to be adapted for a given problem. It is helpful to think of the coefficients $\{C_0, \ldots, C_k\}$ as a filter. The filter, or coefficients, are placed in a transformation matrix that is applied to a raw data vector. The coefficients are ordered using two dominant patterns, one that works as a smoothing filter (like a moving average), and one pattern that works to bring out the data's "detail" information.

The matrix of the DWT may be applied in a hierarchical algorithm, sometimes termed a pyramidal algorithm. The wavelet coefficients are arranged so that odd rows contain an ordering of wavelet coefficients that act as the smoothing filter, and the even rows contain an ordering of wavelet coefficients with different signs that act to bring out the data's detail. The matrix is first applied to the original, full-length vector. Then the vector is smoothed and "decimated" by half and the matrix is applied again. Then the smoothed, halved vector is smoothed, and halved again, and the matrix applied once more. This process continues until a trivial number of "smooth-smooth-smooth . . . " data remain. That is, each matrix application brings out a higher resolution of the data while at the same time smoothing the remaining data. The output of the DWT consists of the remaining "smooth" components, and all of the accumulated "detail" components.

In general, the DWT matrix is not sparse, so it has complexity similar to a discrete Fourier transform. As for the FFT, complexity is addressed by factoring the DWT into a product of a few sparse matrices using self-similarity properties. The result is an algorithm that requires only an order of n operations to transform an n-sample vector. This is the "fast" DWT of Mallat and Daubechies.

The wavelet transform is a subset of a far more versatile transform, the wavelet packet transform. Wavelet packets, identical to nodes in the trees of the '299 patent, are particular linear combinations of wavelets. They form bases that retain many of the properties of their parent wavelets such as orthogonality, smoothness, and localization. Their coefficients are computed by a recursive algorithm, making each newly computed wavelet packet coefficient sequence the root of its own analysis tree.

Because there is a choice among an infinite set of basis functions, one desires to find the best basis function for a given representation of a signal. A "basis of adapted waveform" is the "best basis" function for a given signal representation. The chosen basis carries substantial information about the signal, and if the basis description is efficient (that is, very few terms in the expansion are needed to represent the signal), then that signal information has been compressed. Some desirable properties for adapted wavelet bases (using the basis of adapted waveform) are:

fast computation of inner products with the other basis functions;

fast superposition of the basis functions;

good spatial localization, so one may identify the position of a signal that is contributing a large component;

good frequency localization, so one may identify signal oscillations; and independence, so that not too many basis elements match the same portion of the signal; i.e., minimal overlap or redundancy.

For adapted waveform analysis, one seeks a basis in which the coefficients, when rearranged in decreasing order, decrease as rapidly as possible. To measure rates of decrease, one uses tools from classical harmonic analysis including calculation of information cost functions. This is defined as the expense of storing the chosen representation. Examples of such functions include the number above a threshold, concentration, Shannon's entropy, logarithm of energy, Gauss-Markov calculations, and the theoretical dimension of a sequence. A preferred embodiment of the present invention uses Shannon's entropy.

The '299 patent uses a library of modulated wavelet packets, i.e., combinations of dilations (as related to time) and translations (as related to space) of a wavelet, that are efficient in providing both temporal and spatial localization.

Steps include: applying combinations of dilations and translations to the input signal to obtain processed values; computing the information costs of the processed values; selecting, as encoded signals, an orthogonal group of processed values, the selection being dependent on the computed information costs; and decoding the encoded signals to obtain an output signal. Ideally, the wavelets selected have a reasonable number of vanishing moments. The step of applying combinations of dilations and translations of the wavelet, i.e., wavelet packets, to the input signal comprises correlating combinations of dilations and translations of the wavelet with the signal of interest.

Applying wavelet packets to a signal of interest to obtain processed values includes generating a tree of processed values. The tree has successive levels obtained by applying to the signal of interest, for a given level, wavelet packets that are combinations of the wavelet packets applied at a previous level. The steps of computing information costs and selecting an orthogonal group of processed values include computing at a number of different levels of the tree, and selecting from among the different levels of the tree to obtain an orthogonal group having a minimal information cost, i.e., the "best basis" or "best tree" solution. The step of selecting an orthogonal group of processed values includes generating encoded signals that represent the processed values associated with their respective locations in the tree. These techniques may be adapted to any number of applications including detection of small amounts of elements in material.

If a minute amount of foreign material, e.g., a contaminant, is present in a material, a conventionally generated optical spectra of the contaminated version of the material may appear very similar to that of the non-contaminated version. Thus, without an analytic method yielding very precise measurements, dissembled change is not identified or even detected. Notably, these analyses will be greatly compromised if the available spectra data are noisy. Another drawback inherent in the straightforward use of non-wavelet packet data handling techniques is the requirement for use of a specific resolution based on the material being analyzed. More importantly, even when these techniques are able to detect the presence of contamination, they are not able to localize it, i.e., provide a spatial measure. Accordingly there is a need for an efficient, low cost technique that is somewhat independent of detector resolution, requires no updating to optimize parameters, and provides a reliable spatial measure along with spectral detection and classification.

SUMMARY

A preferred embodiment of the present Invention establishes a fast and efficient technique to detect, localize, and classify small amounts of an element, e.g., contamination that may be present in material. It may be used to analyze any material, including those in the form of liquids, solids, and gases, and to include specifically gels, pastes, hard powders, soft powders, films, inorganics, and pharmaceuticals.

In a preferred embodiment, the technique detects, identifies, and localizes small amounts of particular elements, e.g., contaminants, in a tested sample of material. Data sets, suitable for characterizing components of samples at least spectrally and spatially, are collected from at least one uncontaminated sample of material (the "baseline" or "control") and a sample of material under test (MUT) that may contain contaminants. Preferably, multiple uncontaminated samples are used. Using a preferred embodiment of the present invention to compare the data set from the sample of MUT to the data set(s) collected from the control (s), even minute amounts of contaminants are detected, identified and localized within the MUT.

Generally, the use of Principle Components Analysis (PCA) as an implementing tool in a preferred embodiment of the present invention is established by defining the "components of the tool" as may be used in a preferred embodiment of the present invention, i.e., the covariance matrix, eigenvalues, eigenvectors and the explained values.

Let $x_1$ and $x_2$ be two sets of data with n observed values (or samples) of each. Furthermore let these sets be a description of the same function. Then:

$\bar{x}_1$=mean of the first set
$\bar{x}_2$=mean of the second set
or in vector form:

$$\bar{x} = \begin{bmatrix} \bar{x}_1 \\ \bar{x}_2 \end{bmatrix} \qquad (4)$$

and the covariance matrix is given by:

$$S = \begin{bmatrix} s_1^2 & s_{12} \\ s_{12} & s_2^2 \end{bmatrix} \qquad (5)$$

where:
$s_i^2$=variance;
covariance is given by:

$$s_{12} = \frac{n \sum x_{1k} x_{2k} - \sum x_{1k} \sum x_{2k}}{n(n-1)} \qquad (6)$$

k=index value over the entire number of samples, n;
$x_{1k}$=the $k^{th}$ observation from the first set; and
$x_{2k}$=the $k^{th}$ observation from the second set
This matrix explains the relationship between the "ways" that both sets of data, $x_1$ and $x_2$, describe the same function. The eigenvalues, $\lambda_1$ and $\lambda_2$, are found from solving:

$$\left\| \begin{bmatrix} s_1^2 & s_{12} \\ s_{12} & s_2^2 \end{bmatrix} - \lambda \begin{bmatrix} 1 & 0 \\ 0 & 1 \end{bmatrix} \right\| = \begin{bmatrix} 0 \\ 0 \end{bmatrix} \qquad (7)$$

The eigenvalues are used to characterize the "ways" that both sets of data, $x_1$ and $x_2$, describe the same function.
The eigenvector, $$\begin{bmatrix} u_{11} \\ u_{21} \end{bmatrix},$$

that corresponds to $\lambda_1$ is found from solving:

$$\left\| \begin{bmatrix} s_1^2 & s_{12} \\ s_{12} & s_2^2 \end{bmatrix} - \lambda_1 \begin{bmatrix} 1 & 0 \\ 0 & 1 \end{bmatrix} \right\| \begin{bmatrix} t_{11} \\ t_{21} \end{bmatrix} = \begin{bmatrix} 0 \\ 0 \end{bmatrix} \qquad (8)$$

where:

$$\begin{bmatrix} u_{11} \\ u_{21} \end{bmatrix} = \frac{t_{11}}{\sqrt{\begin{bmatrix} t_{11} & t_{21} \end{bmatrix} \begin{bmatrix} t_{11} \\ t_{21} \end{bmatrix}}} \begin{bmatrix} t_{11} \\ t_{21} \end{bmatrix} \qquad (9)$$

and the eigenvector, $$\begin{bmatrix} u_{12} \\ u_{22} \end{bmatrix},$$

that corresponds to $\lambda_2$ is found from solving:

$$\left\| \begin{bmatrix} s_1^2 & s_{12} \\ s_{12} & s_2^2 \end{bmatrix} - \lambda_2 \begin{bmatrix} 1 & 0 \\ 0 & 1 \end{bmatrix} \right\| \begin{bmatrix} t_{12} \\ t_{22} \end{bmatrix} = \begin{bmatrix} 0 \\ 0 \end{bmatrix} \qquad (10)$$

where:

-continued $$\begin{bmatrix} u_{12} \\ u_{22} \end{bmatrix} = \frac{t_{12}}{\sqrt{[t_{12} \ t_{22}] \begin{bmatrix} t_{12} \\ t_{22} \end{bmatrix}}} \begin{bmatrix} t_{12} \\ t_{22} \end{bmatrix} \quad (11)$$

The eigenvalues are used to characterize the "ways" that both sets of data describe the same function.

Explained values are often provided as percents, such as:

percent explained corresponding to $\lambda_1$ is $$\frac{\lambda_1}{\lambda_1 + \lambda_2} \times 100$$

and percent explained corresponding to $\lambda_2$ is $$\frac{\lambda_2}{\lambda_1 + \lambda_2} \times 100.$$

The explained values are used to show which "way" has more "impact" on the description of the function.

At each observation data values from the two sets of data, $x_1$ and $x_2$, are paired, e.g., $(x_{11}, x_{21})$, $(x_{12}, x_{22})$ ... $(x_{1n}, x_{2n})$. In the first pair $x_{11}$ represents the data value at the first observation from the first set, $x_1$, and $x_{21}$ represents the data value at the first observation from the second set, $x_2$, and so on. To find the principal components, i.e., $z_{11}$ and $z_{21}$, that correspond to the first observation, the following is solved:

$$\begin{bmatrix} z_{11} \\ z_{12} \end{bmatrix} = \begin{bmatrix} u_{11} & u_{12} \\ u_{21} & u_{22} \end{bmatrix} \begin{bmatrix} x_{11} & -\bar{x}_1 \\ x_{21} & -\bar{x}_2 \end{bmatrix} \quad (12)$$

This computation is repeated for each individual pair of observations. Note that $\lambda_1$ and its "explained value" correspond to $z_{11}$. As well, $\lambda_2$ and its explained value correspond to $z_{21}$. Thus, principal components corresponding to each observation are known.

In general, the Q-value that corresponds to the first observation is computed as:

$$Q_1 = z_{11}^2 + z_{21}^2 \quad (13)$$

This PCA is repeated for every observation. In the case where m sets of data are used to describe the same function, the Q-value that corresponds to the first observation is $$z_{11}^2 + z_{21}^2 + z_{31}^2 + z_{41}^2 + \ldots + z_{m1}^2.$$

Most importantly, however, it may be desirable to truncate this sum before reaching the $$z_{m1}^2$$

term, depending on the value of the percent explained that corresponds to each term. The higher the value of the "percent explained" the more likely the corresponding "z-term" is included in the summation used to estimate the Q-value. Once the Q-value at each observation is computed, these values are compared against a Q-limit.

For j selected terms, Q-limit is computed as:

$$\theta_1 = \sum_{i=1}^{j} l_i \quad (14)$$

$$\theta_2 = \sum_{i=1}^{j} l_i^2 \quad (15)$$

$$\theta_3 = \sum_{i=1}^{j} l_i^3 \quad (16)$$

$$h_0 = 1 - \frac{2\theta_1 \theta_3}{3\theta_2^2} \quad (17)$$

$$Q = \theta_1 \left[ \frac{ch_0 \sqrt{2\theta_2}}{\theta_1} + \frac{\theta_2 h_0 (h_0 - 1)}{\theta_1^2} + 1 \right]^{\frac{1}{h_0}} \quad (18)$$

where:

Q=Q-limit;

c=an approximately normally distributed function with zero mean and unit variance; and $l_i$=the $i^{th}$ eigenvalue.

Using the PCA operation described above in a preferred embodiment of the present invention, Q-values greater than the Q-limit indicate the existence of contamination, albeit trace amounts of contamination in many cases of interest to the investigator.

In general, the method involves:

decomposing the data sets from the MUT and the control by applying a pre-specified wavelet family to each data set;

generating corresponding wavelet-packets (WPs) for each decomposed data set using an appropriate criterion, such as the Shannon entropy criterion;

generating a "best tree" for each WP, the best tree having nodes, each best tree representing a WP corresponding to each decomposed data set;

generating a "branching/non-branching" operation on each best tree to establish a basis for comparison of the nodes of the best trees;

comparing the nodes from the branching/non-branching operation to identify for further processing only mismatched pairs of the nodes such that a mismatched pair comprises a node that branches in one best tree (MUT) and does not branch in another best tree (Control), or vice versa;

using a principal component analysis, for each mismatched pair thus identified, placing the data from the Control data set corresponding to a same node taken from at least one control sample, but preferably from multiple control samples, in a first data file;

generating a covariance matrix for this first data file from which eigenvectors, eigenvalues and "explained value" (or "percent explained") vectors are derived;

adding only the data associated with a same node from the first data set to the first data file to obtain a second data file from which eigenvectors, eigenvalues and explained value vectors are derived, generating a Q-Limit to compare the first and second data files to a pre-specified threshold;

finding residuals of the second data file;

using the residuals, computing corresponding Q-Values, such that if the corresponding Q-values are higher than the calculated Q-Limit, this indicates existence of particular contaminants in the MUT at each location at which the particular material is observed.

More particularly, a preferred embodiment uses inputs from interferograms in a method that detects, classifies and spatially locates minor amounts of an undesired element in a sample of a material under test (MUT). The characteristics of this sample of MUT are taken from an interferogram as are "control" uncontaminated samples of the same material. These control samples are prepared in advance and known to contain none of the undesired element. The method involves:

developing a first best tree using a MUT wavelet-packet best tree operation to decompose the interferogram of the sample of the MUT using a pre-specified family of wavelets in which corresponding wavelet-packets are generated;

using a suitable criterion such as the Shannon entropy criterion, providing a first output as a set of signals of wavelet-packets MUTWP1, MUTWP2, . . . MUTWPN, where N is a whole number >0;

developing a second best tree using a non-contaminated sample (NCS) wavelet-packet best tree operation to decompose the interferogram of a first control sample, NCS1;

using a specified family of wavelets in which corresponding wavelet-packets are generated employing a suitable criterion such as the Shannon entropy criterion, providing a second output as a set of signals of wavelet-packets NCS1 WP1, NCS1 WP2, NCS1 WP3, . . . , NCS1 WPK, where K is a whole number >0;

performing a third operation on these first and second outputs with a branching/non-branching wavelet-packet operation, such that corresponding wavelet-packets of the best trees generated by the MUT wavelet packet best tree operation and the sample wavelet packet best tree operation are compared to determine if both wavelet-packets either branch or do not branch;

selecting those pairs that are not matched, i.e., one wavelet packet branches and the other does not branch;

outputting those pairs as a set of signals of mismatched wavelet-packet pairs:

[(non-contaminated sample number one mismatched wavelet-packet one (NCS1 MMWP1), material under test mismatched wavelet-packet number one (MUTMMWP1)], (NCS1 MMWP2, MUTMMWP2), . . . (NCS1 MMWPR, MUTMMWPR), where R is a whole number >0;

performing a fourth operation by reusing results from the first operation above and repeating the next two operations for each of the available control samples (non-contaminated samples), so that corresponding mismatched wavelet-packet pairs are generated for each of the available control samples;

using the corresponding mismatched wavelet packet pairs to populate a table of MUT Mismatched Wavelet-packets (MMWP) vs. Corresponding Non-contaminated Sample Mismatched Wavelet-packets (NCSMMWP);

performing a fifth operation on NCS1 MMWP1, NCS2 MMWP1, . . . NCSJMMWP1 using a Non-Contaminated Sample Principal Component Analysis Operation (NCSPCAO), such that a first covariance matrix is generated;

further by employing the first covariance matrix to generate matrices of eigenvectors, eigenvalues and "explained value" vectors, outputting mismatched packet eigenvectors, mismatched packet eigenvalues, and "mismatched packet explained values;" and performing a sixth operation on the output of the fifth operation with a Non-Contaminated Sample Q-Limit Operation computing a Q-Limit, NCSQLO, such that for a first non-contaminated sample, the output of the sixth operation is an NCS1 Q-Limit, for a second non-contaminated sample, the output of the sixth operation is an NCS2 Q-Limit, and continuing through the number of non-contaminated samples available;

performing a seventh operation on mismatched pairs of a first wavelet packet of a first sample for each non-contaminated sample MUTMMWP1 and NCS1 MMWP1, and NCS2 MMWP1, . . . , and NCSJM-MWP1 with a MUT Principal Component Analysis Operation (MUTPCAO), generating a second covariance matrix;

from the second covariance matrix, generating corresponding second matrices of second eigenvectors, second eigenvalues and second "explained" vectors;

outputting a set of MUT principal components (MUTMMWP1 PC); and performing an eighth operation on the MUTMMWP1PC with a MUT Q-Value Operation (MUTQVO), providing MUTMMWP1 PC-Q-Values;

generating residuals from the MUTMMWP1 PC-Q-Values;

comparing the residuals from the MUTMMWP1 PC-Q-Values, such that MUTMMWP1 PC-Q-Values greater than the NCS1 Q-Limit indicate localized contamination in the MUT corresponding to row 1 of the generated table of values; and performing a ninth operation similar to the fifth operation for the information in the $2^{nd}$ column-$2^{nd}$ row, $2^{nd}$ column-$3^{rd}$ row, . . . , and $2^{nd}$ column-$R^{th}$ row of the table of values, such that NCS2 Q-Limit, NCS3 Q-Limit, . . . , NCSRQ-Limit are generated;

repeating the seventh operation for the information in the $2^{nd}$ row, $3^{rd}$ row, $4^{th}$ row . . . . and $R^{th}$ row of the table of values, such that the MUTMMWP2 PC-Q-Values, MUTMMWP3 PC-Q-Values, MUTMMWP4 PC-Q-Values, . . . , MUTMMWPRPC-Q-Values are generated, and comparing the MUTMMWPXPC-Q-Values with the NCSXQ-Limit, where X=2, 3, 4, . . . , R, such that all corresponding localized appearances of minor amounts of an element in the first MUT sample are identified, classified, and localized, and to provide a visual cue of the difference between the non-contaminated control samples and the MUT, in a manner similar to the third operation above, the corresponding wavelet-packet signal NCS1 MMWP1 of the known sample is added to the data file accumulated in the first operation to form a new data file. The residuals of this new data file are computed and used to generate a "Q-Values without contamination" curve.

Of course, for multiple samples of material under test, the process is repeated for each sample. Thus, advantages of a preferred embodiment of the present invention include:

provides improved encoding and decoding of data;

offers improved efficiency of operation by eliminating the need for taking data with multiple instrumentation configurations;

inexpensive to operate;

reduces man-hours to implement;

improves speed of analysis;

improves accuracy;

operates independently of detector resolution;

requires no updating to optimize parameters;

improves reliability in detection and classification;

provides the ability to localize in both wave number and space domains;

provides for easy implementation; and provides for ease of automation.

DETAILED SPECIFICATION

Figure 1:
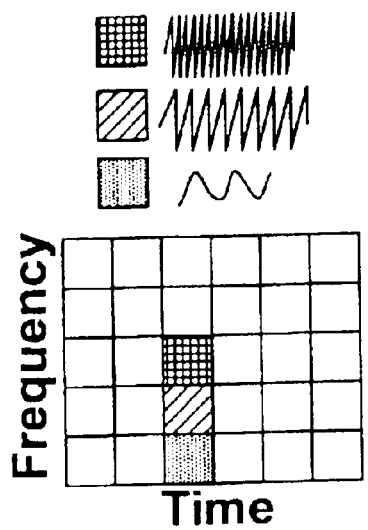
FIG. 1 depicts frequency versus time for a Fourier Transform representation of signals of different frequencies.
Figure 2:
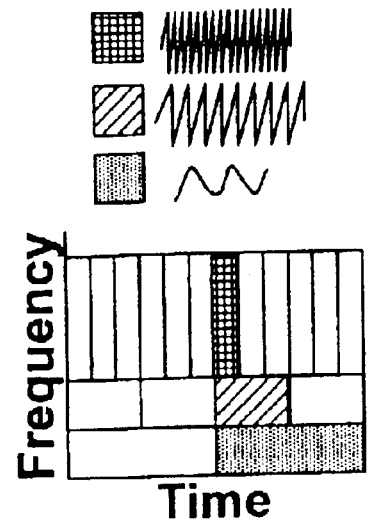
FIG. 2 depicts frequency versus time for a Digital Wavelet Transform (DWT) representation of signals of different frequencies.
Figure 3:
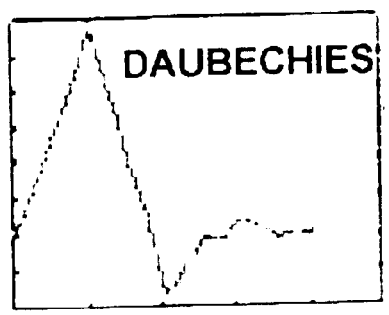
FIG. 3 illustrates four separate DWT families.
Figure 3:
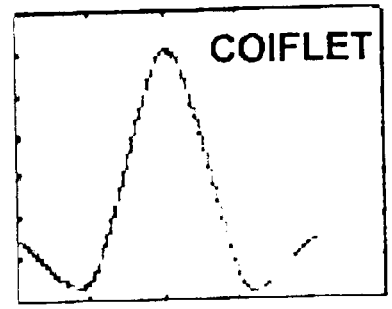
Figure 3:
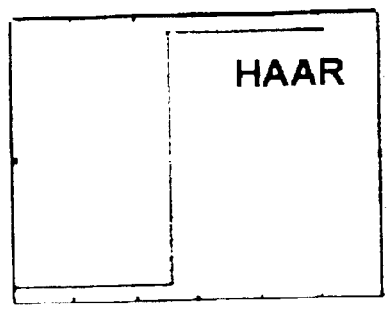
Figure 3:
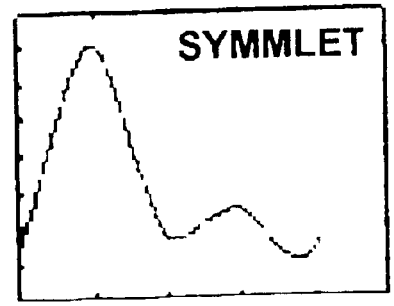
Figure 4:
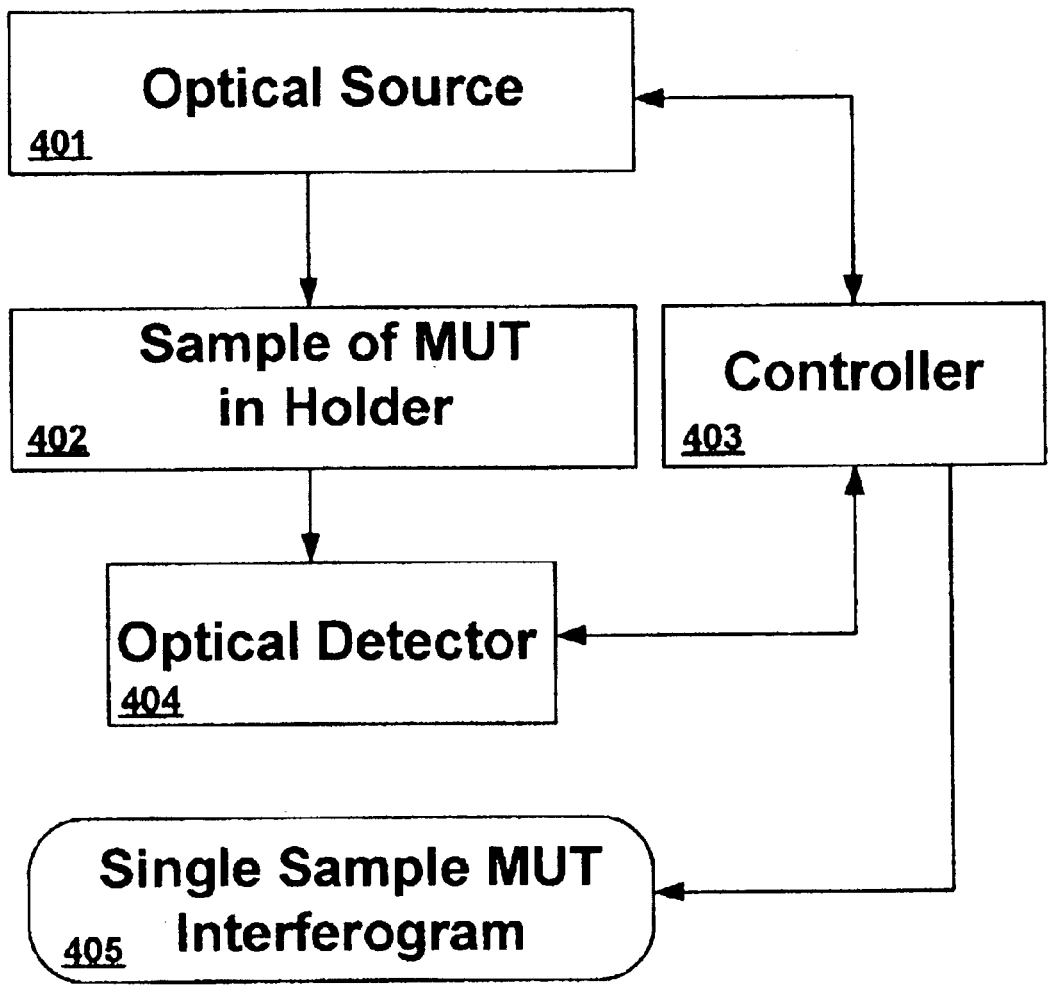
FIG. 4 is a block diagram of an interferometer for generating the desired interferograms to be used in a preferred embodiment of the present invention.

Refer to FIG. 4. To collect data necessary for processing, one may use a configuration that includes an optical source 401, a sample holder 402, a controller 403, and an optical detector 404. The output from this setup is an interferogram 405 of either a sample of material of unknown composition under test (MUT) or a known sample, preferably a non-contaminated sample (NCS).

Figure 5:
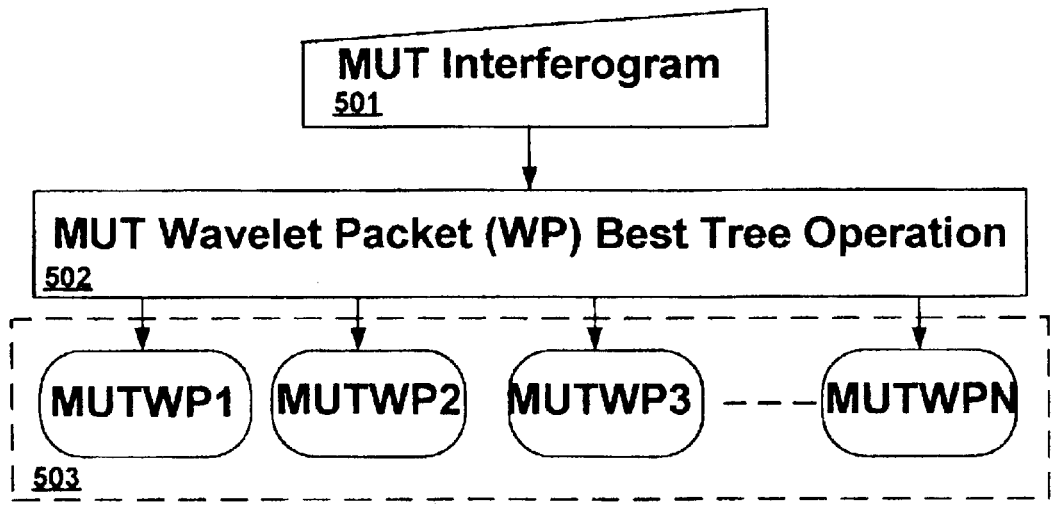
FIG. 5 is a block diagram of signal processing steps that yield wavelet packets when applied to the interferogram of material under test (MUT).

In operation, to classify a sample of a MUT for contamination, J non-contaminated samples (NCS1, NCS2, . . . , NCSJ) of the same material are prepared and the following steps are performed:

Step 1. Refer to FIG. 5. An interferogram for an unknown material composition, e.g., a MUT interferogram 501, is operated on by a MUT wavelet-packet best tree operation 502 and its best tree is developed. The interferogram 501 is decomposed using a family of selected wavelets and corresponding wavelet-packets are generated using the Shannon entropy criterion, established in the relationship $$H_n(p_1, p_2, \ldots, p_n) = -\sum_{i=1}^{n} p_i \log_2 p_i \tag{19}$$

Let x be a discrete random variable taking a finite number of possible values $x_1, x_2, \ldots x_n$ with probabilities $p_1, p_2, \ldots, p_n$, respectively such that $p_i \geq 0, i=1, 2, \ldots, n$ and $$\sum_{i=1}^{n} p_i = 1;$$

a number is established that will measure the amount of uncertainty; given that h is a function defined on the interval [0,1] and h(p) is interpreted as the uncertainty associated with the event $x=x_i$, $i=1, 2, \ldots, n$, i.e., the information conveyed by revealing that x has taken on the value $x_i$ in a given performance of the experiment.

For each n, define a function $H_n$ of the n variables $p_1, p_2, \ldots, p_n$. The function $H_n(p_1, p_2, \ldots, p_n)$ is the average uncertainty associated with the event $\{X=x_i\}$, $i=1,2, \ldots, n$ given by $$H_n(p_1, p_2, \ldots, p_N) = \sum_{i=1}^{N} p_i h(p_i) \tag{20}$$

Thus $H_n(p_1, p_2, \ldots, p_n)$ is the average uncertainty removed by revealing the value of X. For simplicity denote $$\Delta_n = \left\{ P = (p_1, p_2, \ldots, p_n); p_i \geq 0, \sum_{i=1}^{n} p_i = 1 \right\} \tag{21}$$

Let X and Y be two independent experiments with n and m values respectively. Let $P=(p_1, p_2, \ldots, p_n) \in \Delta_n$ be a probability distribution associated with X and $Q=(q_1, q_2, \ldots, q_m) \in \Delta_m$ be a probability distribution associated with Y. This leads to $$H_{nm}(P*Q) = H_n(P) + H_m(Q) \tag{22}$$

for all $P=(p_1, p_2, \ldots, p_n) \in \Delta_n$, $Q=(q_1, q_2, \ldots, q_m) \in \Delta_m$ and $P*Q=(p_1q_1, \ldots p_1q_m, p_2q_1, \ldots, p_2q_m, \ldots, p_nq_1, \ldots, p_nq_m) \in \Delta_{nm}$.

Replacing $p_i h(p_i)$ in Eqn. (20) by $f(p_i)$, $\forall i=1,2,\ldots,n$, yields:

$$H_n(P) = \sum_{i=1}^{n} f(p_i) \tag{23}$$

from which Shannon's Entropy function, Eqn.(19), may be derived. Shannon, C. E., *A Mathematical Theory of Communication*, Bell Syst. Tech. J., 27, 379–423, 623–656, 1948.

[In addition to the Shannon Entropy other criteria, i.e., types of entropies, may be used in embodiments of the present invention. Examples of some are listed below. In what follows, a signal, s, has coefficients, $s_i$, of s in an orthonormal basis. Entropy, H, is an additive construct such that:

$$H(0) = 0 \tag{24}$$

and $$H(s) = \Sigma_i H(s_i) \tag{25}$$

Accordingly examples of forms of entropy that may be used in embodiments of the present invention include:

The Shannon Entropy that may be described by:

$$H(s) = -\sum_i s_i^2 \log(s_i^2) \tag{26}$$

where:

the entropy of the $i^{th}$ single coefficient is given by:

$$H(s_i) = -s_i^2 \log(s_i^2) \tag{27}$$

with the convention:

$$0\log(0) = 0 \tag{28}$$

the concentration in $\rho$ norm with $1 \leq \rho$, by:

$$H(s) = \Sigma_i |s_i|^\rho \tag{29}$$

where the entropy of the $i^{th}$ single coefficient is given by:

$$H(s_i) = |s_i|^\rho \tag{30}$$

and the logarithm of the "energy" by:

$$H(s) = \sum_i \log(s_i^2) \tag{31}$$

where:

the entropy of the $i^{th}$ single coefficient is given by:

$$H(s_i) = \log(s_i^2) \tag{32}$$

with the convention $$\log(0) = 0$$

The Threshold Entropy, H(s), that may be described as the number of time instants when the signal is greater than a threshold, $\epsilon$, where the entropy of the $i^{th}$ single coefficient is given by:

$$H(s_i) = \begin{cases} 1 & |s_i| > \epsilon \\ 0 & \text{Otherwise} \end{cases} \tag{33}$$

and

The Sure Entropy described as:

$$H(s) = \sqrt{2\log_{e[n\log_2(n)]}} \tag{34}$$

where n is the number of samples in s. Coifman, R. R.; M. V Wickerhauser (1992), *Entropy-based Algorithms for Best Basis Selection*, IEEE Trans. on Info. Theory, Vol. 38, 2, pp. 713–718.

The output from this operation is a set of signals of wavelet-packets MUTWP1, MUTWP2, . . . , MUTWPN 503, where N is a positive whole number.

Figure 6:
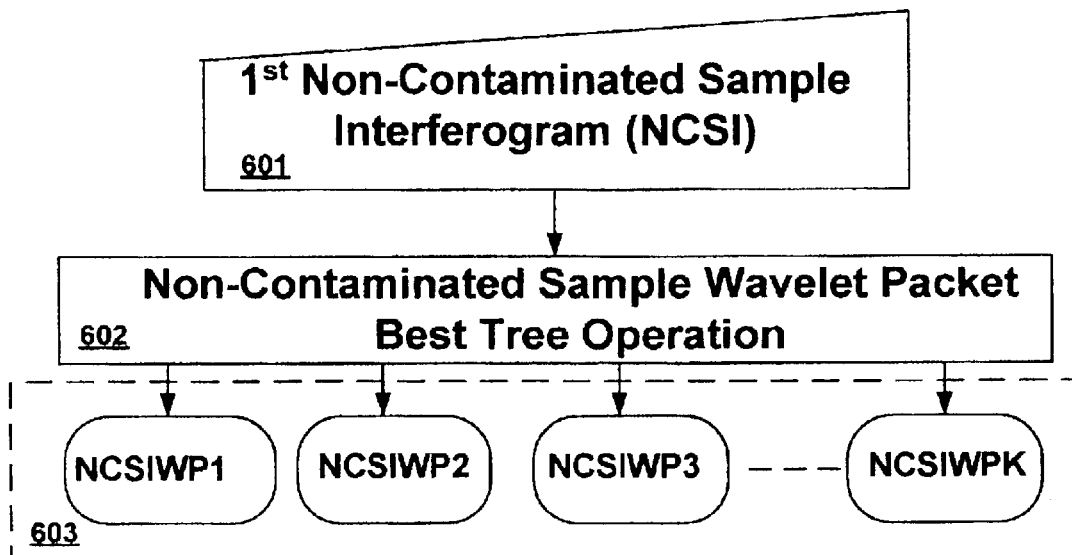
FIG. 6 is a block diagram of signal processing steps that yield wavelet packets when applied to the interferogram of known samples.

Step 2. Refer to FIG. 6. The interferogram of the first known sample, e.g., a non-contaminated sample (NCS1) 601, is operated on by a non-contaminated sample wavelet-packet (NCSWP) best tree operation 602 and its best tree is developed using the Shannon Entropy. The output from this operation is a set 603 of signals of wavelet-packets NCS1WP1, NCS1WP2, NCS1WP3, . . . , NCS1WPK, where K is a positive whole number.

Figure 7:
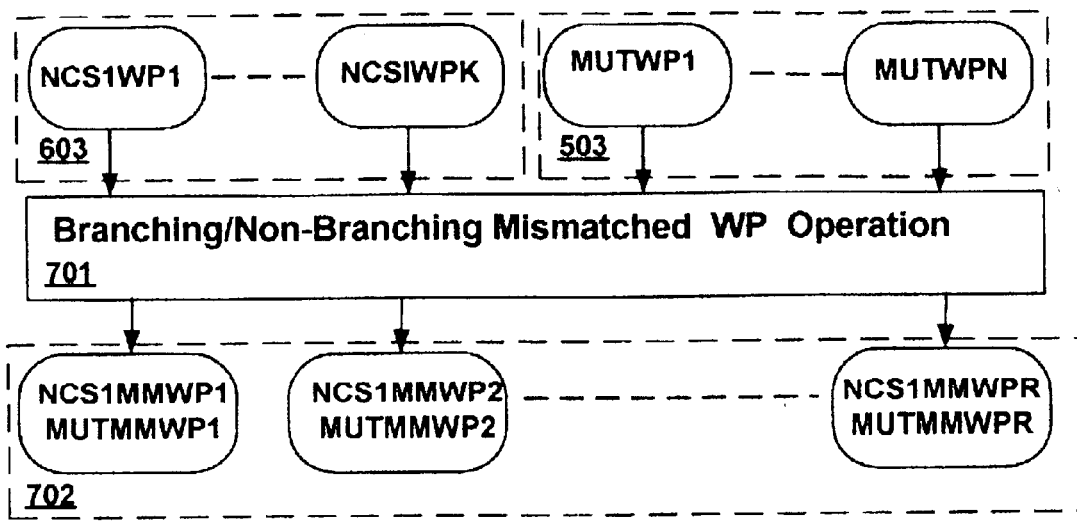
FIG. 7 is a block diagram of signal-processing steps that determine the mismatches (dissimilarities) between the wavelet packets generated by the procedures depicted in FIGS. 5 and 6 with the same wavelet packets generated by both procedures used to form pairs.

Step 3. Refer to FIG. 7. NCS1WP1, NCS1WP2, NCS1WP3, . . . , NCS1WPK 603 along with MUTWP1, MUTWP2, . . . MUTWPN 503 are operated on by a branching/non-branching mismatched wavelet-packet (WP) operation 701. In every pair 603, 503 if and only if (IFF) one member is branching and the other does not branch is the pair declared a mismatch. The output of this operation is a much smaller set of signals comprising only mismatched wavelet-packet pairs 702: (NCS1MMWP1, MUTMMWP1), (NCS1MMWP2, MUTMMWP2), . . . , (NCS1MMWPR, MUTMMWPR), where R is a positive whole number.

Step 4. Results from Step 1 are re-used and Steps 2 and 3 are repeated for every chosen known (non-contaminated) sample and their corresponding mismatched wavelet-packet pairs 702 are generated and used to populate a table. A representative list of these pairs is shown in Table 1.

TABLE 1

Mismatched Wavelet-packets

| MUT MISMATCHED WAVELET-PACKETS | CORRESPONDING NON-CONTAMINATED SAMPLE MISMATCHED WAVELET-PACKETS |
|---|---|
| MUTMMWP1 | NCS1MMWP1, NCS2MMWP1, . . . , NCSJMMWP1 |
| MUTMMWP2 | NCS1MMWP2, NCS2MMWP2, . . . , NCSJMMWP2 |
| MUTMMWP3 | NCS1MMWP3, NCS2MMWP3, . . . , NCSJMMWP3 |
| . | . |
| . | . |
| . | . |
| MUTMMWPR | NCS1MMWPR, NCS2MMWPR, . . . , NCSJMMWPR |

Figure 8:
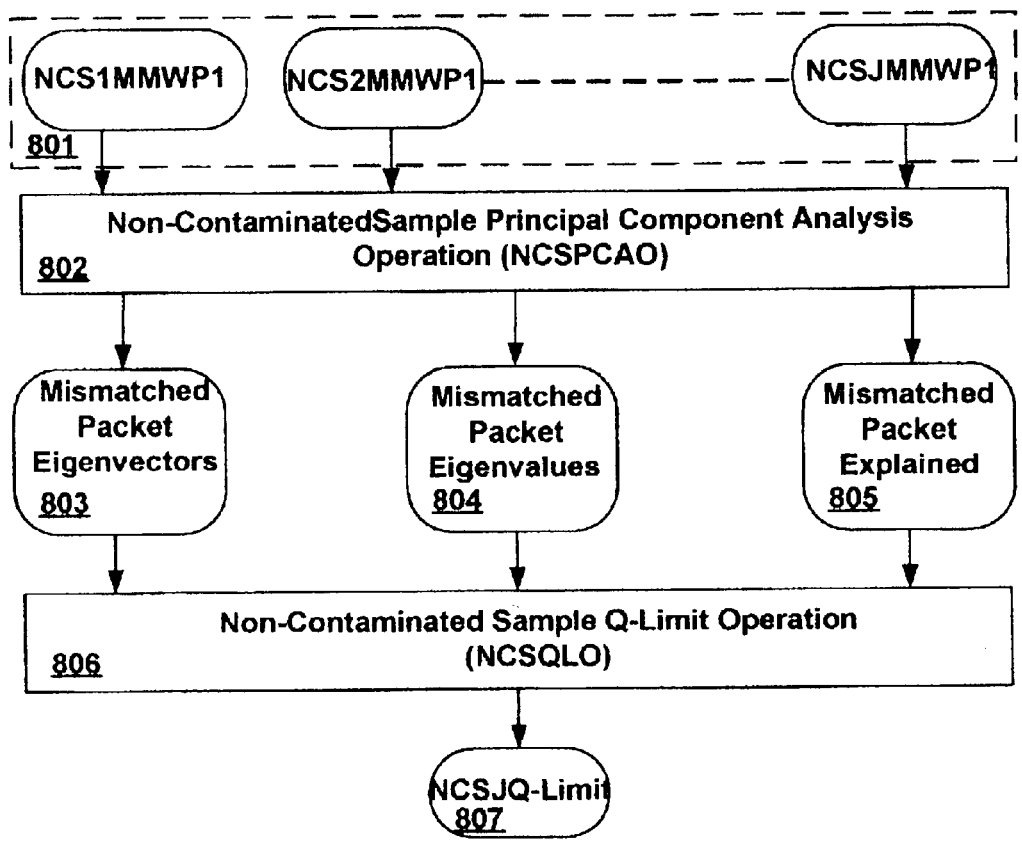
FIG. 8 is a block diagram of steps applied to the mismatched wavelet packets of non-contaminated samples generated by the procedure depicted in FIG. 7.

Step 5. Refer to FIG. 8. The mismatched pairs of the first row of the table, i.e., NCS1MMWP1, NCS2MMWP1, . . . , NCSJMMWP1 801 ($2^{nd}$ column-$1^{st}$ row in Table 1), are operated on by a Non-contaminated Sample Principal Component Analysis Operation (NCSPCAO) 802. For example, data analysis may be performed using standard chemometric methods such as PCA and SIMCA®, which are available in commercial software packages that run on a PC or which are easily transferred into a computer running a resident algorithm or onto a signal analysis chip either integrated onto, or working in conjunction with, the interferometer (sensor) measurement electronics. Commonly used commercially available programs include MATLAB® and MATHEMATICA®. The Fisher Linear Discriminant is one preferred algorithm for analysis of the data. In addition, more sophisticated algorithms and supervised or unsupervised neural network based learning/training methods may be applied as well. Duda, R. O., Hart, P. E., *Pattern Classification and Scene Analysis*, John Wiley & Sons: New York, 1973, p. 482.

The output of this operation includes Mismatched Packet Eigenvectors 803, Mismatched Packet Eigenvalues 804, and Mismatched Packet Explained 805. These outputs are used by a Non-contaminated Sample Q-Limit Operation (NCSQLO) 806 to produce the NCSJQ-Limit 807. Refer to previous discussion on the PCA for a method of producing the Q-LIMIT.

Figure 9:
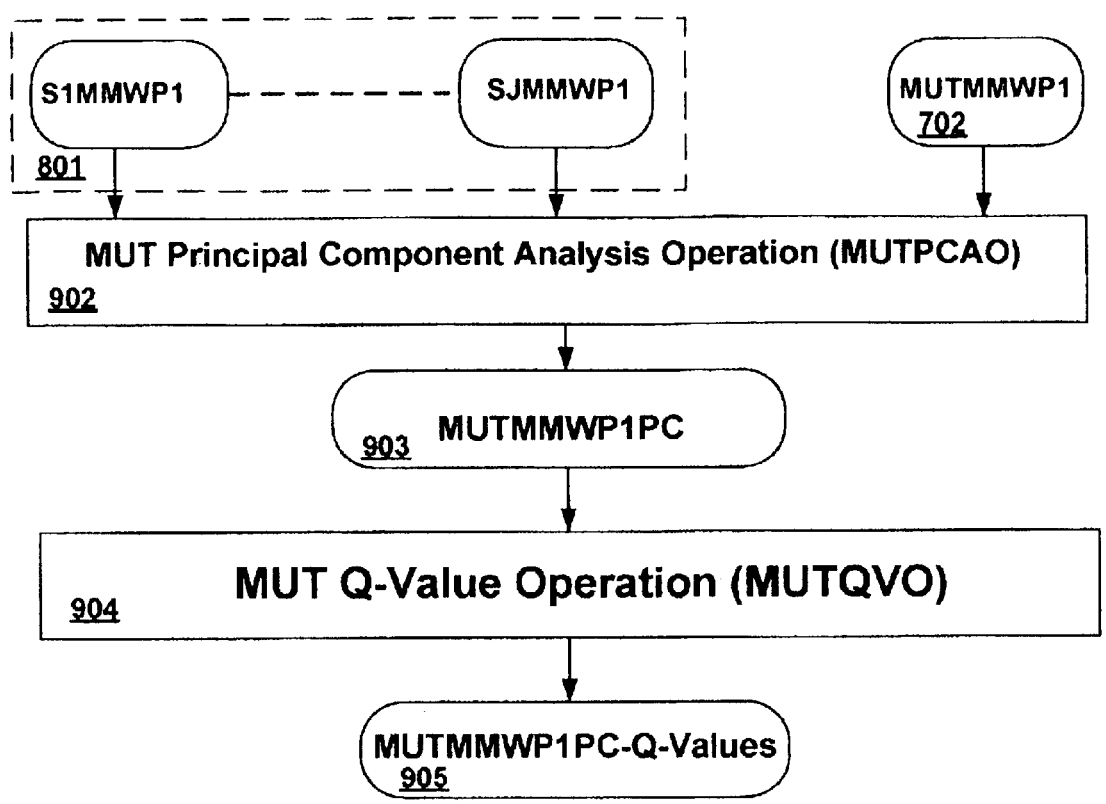
FIG. 9 is a block diagram of steps applied to the mismatched wavelet-packets of non-contaminated samples and a first corresponding MUT mismatched wavelet-packet.
Figure 10A:
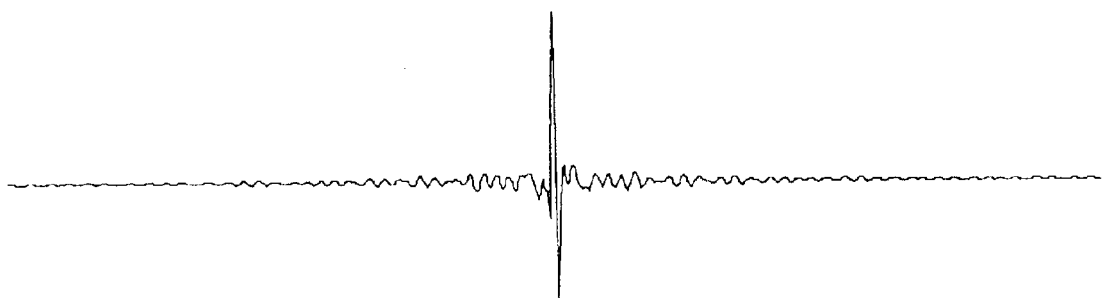
FIG. 10A is an example of an interferogram of a non-contaminated sample.
Figure 10B:
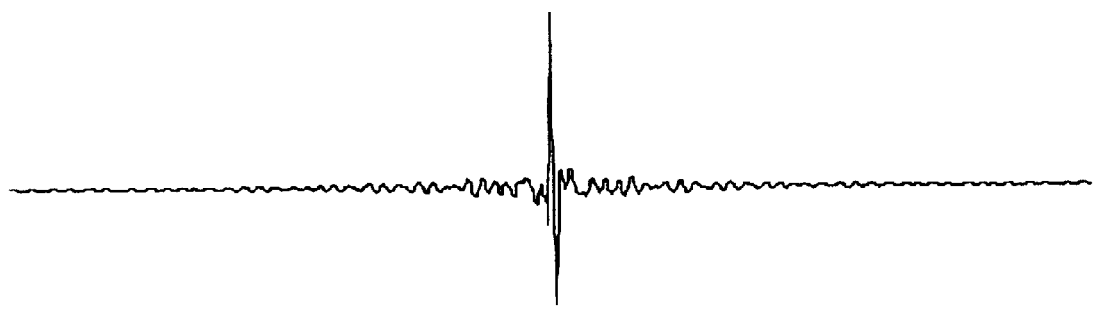
FIG. 10B is an interferogram of a contaminated version of the material depicting how difficult visual differentiation can be.

Step 6. Refer to FIG. 9. MUTMMWP1 702 and NCS1MMWP1, NCS2MMWP1, . . . , NCSJMMWP1 801 ($1^{st}$ row in Table 1) are operated on by a MUT PCA Operation (MUTPCAO) 902. The output of this operation is a set of MUT principal components (MUTMMWP1 PC) 903 that are operated on by a MUT Q-Value Operation (MUTQVO) 904, to yield the MUT-MMWP1 PC-Q-Values 905. MUTMMWP1 PC-Q-Values 905 that are greater than NCSJQ-Limit 807 indicate localized contamination in the MUT that corresponds to the information of the $1^{st}$ row in Table 1. The Q-values are produced as described earlier.

Step 7. Step 5 is repeated for the information in the $2^{nd}$ column-$2^{nd}$ row, $2^{nd}$ column-$3^{rd}$ row, . . . , and $2^{nd}$ column-$R^{th}$ row of Table 1 and the corresponding NCS2Q-Limit, NCS3Q-Limit, NCS4Q-Limit, . . . , and NCSRQ-Limits 807 are generated. The Q-limit values are produced as described earlier.

Step 8. Step 6 is repeated for the information in the $2^{nd}$ row, $3^{rd}$ row, $4^{th}$ row . . . , and $R^{th}$ row of Table 1 and MUTMMWP2 PC-Q-Values, MUTMMWP3 PC-Q-Values, MUTMMWP4 PC-Q-Values, . . . , MUTMMWPRPC-Q-Values 905 are generated. The Q-values are produced as described earlier.

Step 9. MUTMMWPXPC-Q-Values 905 are compared with NCSXQ-Limit 807, where X=2, 3, 4, . . . , R and all corresponding localized contaminants are identified, classified, and localized.

Figure 14:
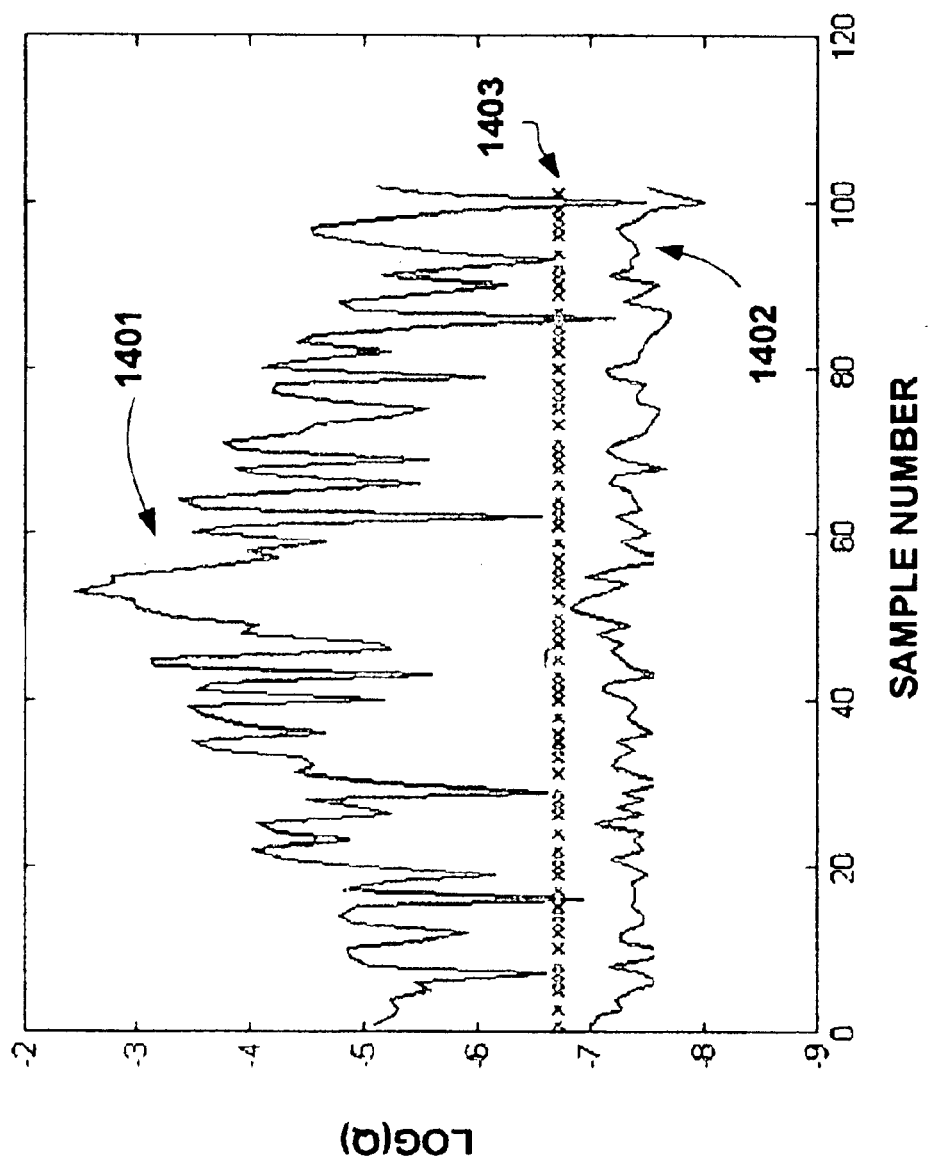
FIG. 14 presents a comparison of Q-Values obtained for samples with and without contamination to a Q-Limit for one mismatched wavelet packet.

The procedure used to generate the Q-Limit 1403 and Q-Values 1401, 1402 curves of FIG. 14 is as follows:

a. NCS2MMWP1, . . . , NCSJMMWP1 801 generated by the procedure depicted in FIG. 8 is accumulated in a data file 801 and using a Non-contaminated Sample PCA Operation 802, a covariance matrix of Mismatched Packet Eigenvectors 803 is generated.

b. The Mismatched Packet Eigenvalues 804 and the Mismatched Packet Explained 805 of the covariance matrix 803 generated in step (a) are generated using principles as described for the PCA above. This information is used to generate NCSJQ-Limit 807 for establishing the Q-Limit curve 1403. Ahmad, F. H. et al., *A Wavelet Packets Technique for the Detection of Anomalies in Fourier Transform Infrared Interferograms*, Spectroscopy Letters, 35(4), pp. 527–541, 2002.

c. The corresponding wavelet-packet signal, MUTM-MWP1 702 of the material under test (MUT), i.e., the potentially contaminated material, is added to the data file accumulated in step (a) 801. Refer to FIGS. 9 and 14. Using the MUT PCA Operation (MUTPCAO) 902 a new data file is formed, MUTMMWP1 PC 903. Using the MUT Q-Value Operation (with a procedure for determining this previously described in the PCA description), (MUTQVO) 904, the residuals of this new data file are computed and used to generate MUTMMWPlPC-Q-VALUES 905 from which the "Q-Values with contamination curve" 1401 is derived. Ahmad (2002).

d. In a manner similar to step (c) above (not shown separately), the corresponding wavelet-packet signal NCS1 MMWP1 of the known sample is added to the data file accumulated in step (a) 801 to form a new data file. The residuals of this new data file are computed and used to generate the "Q-Values without contamination" curve 1402. Ahmad (2002).

EXAMPLE

Figure 11:
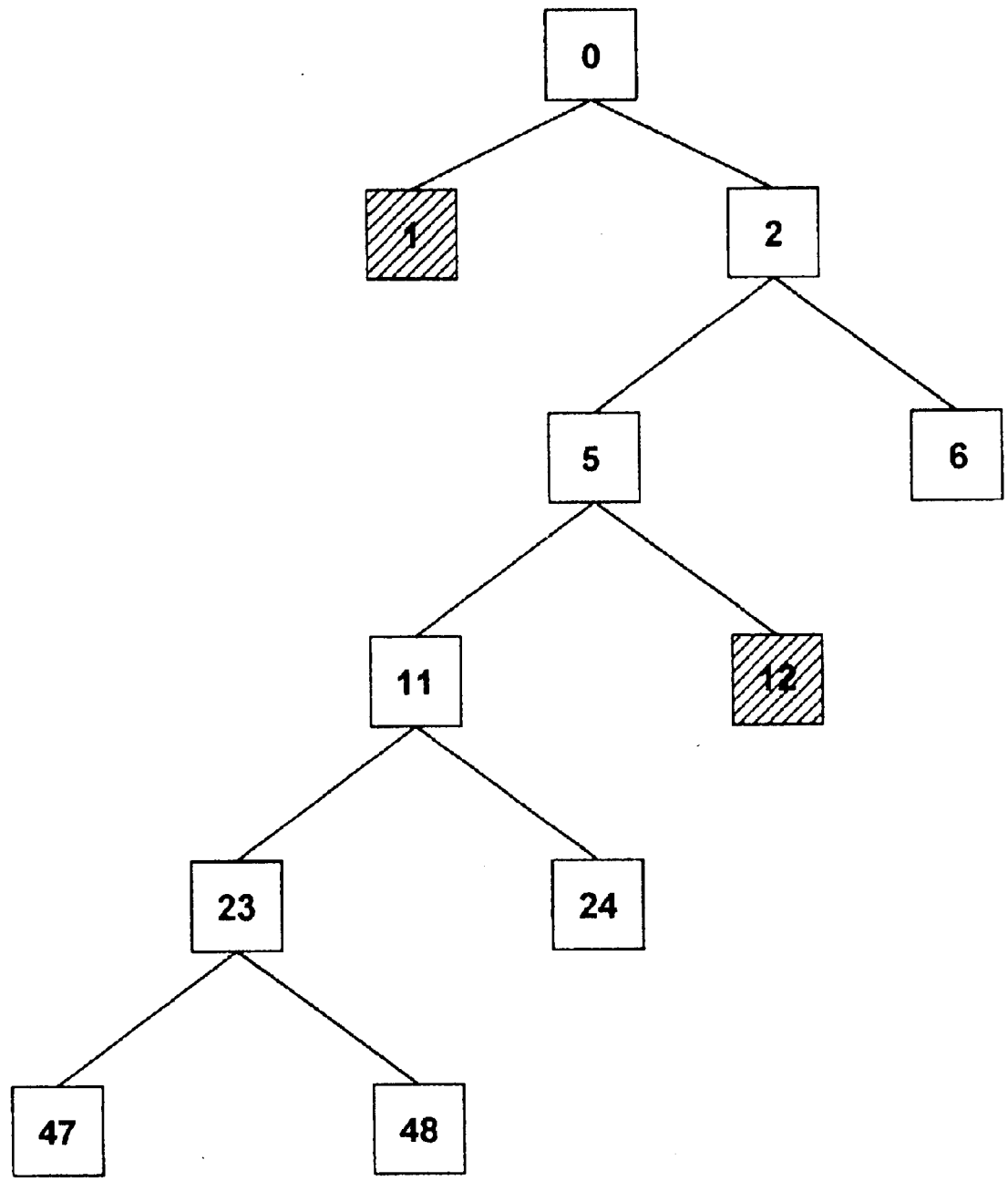
FIG. 11 illustrates the best tree of the interferogram shown in FIG. 10A using the procedure depicted in FIG. 6.
Figure 12:
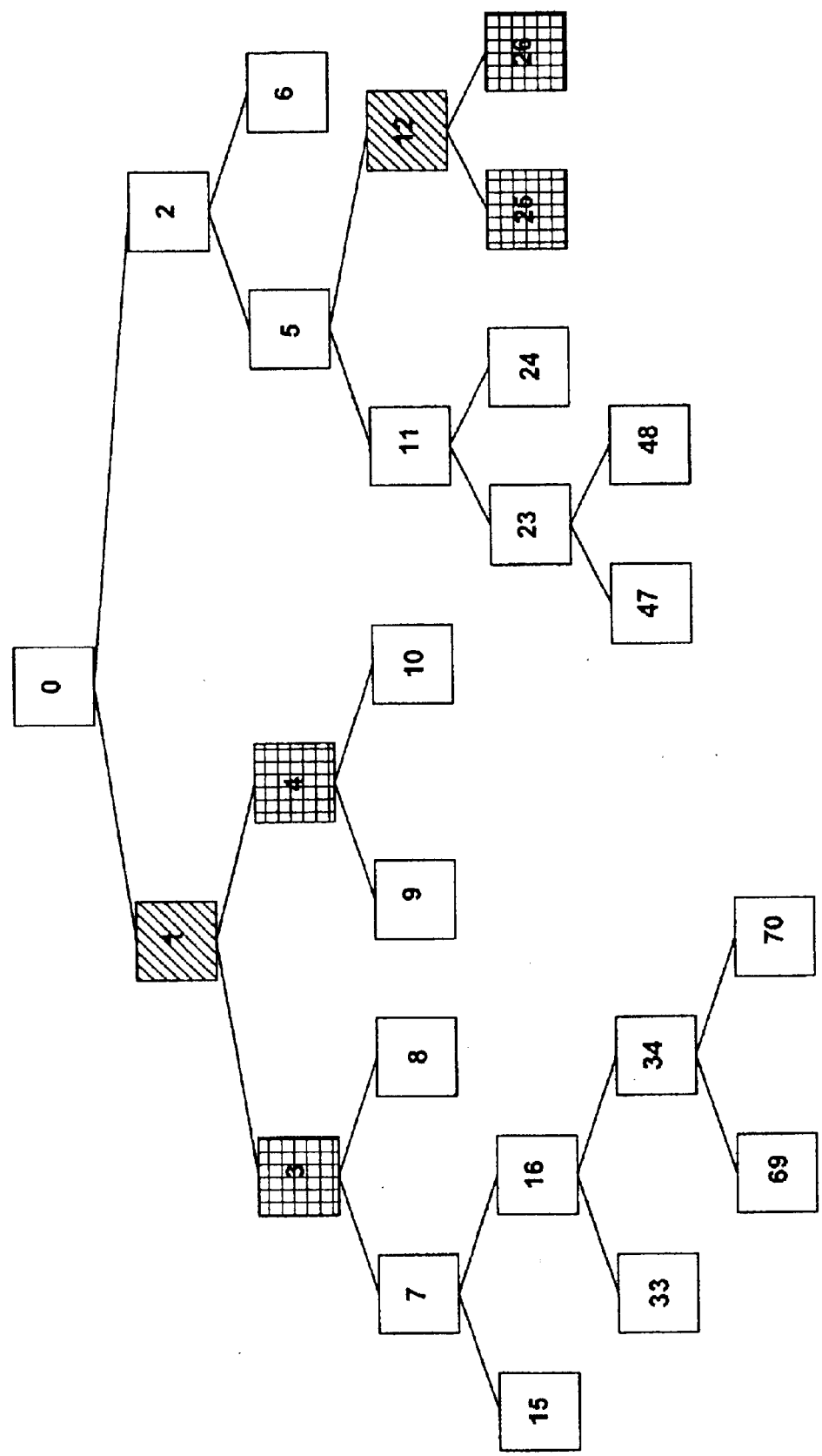
FIG. 12 illustrates the best tree of the interferogram shown in FIG. 10B using the procedure depicted in FIG. 5.
Figure 13A:
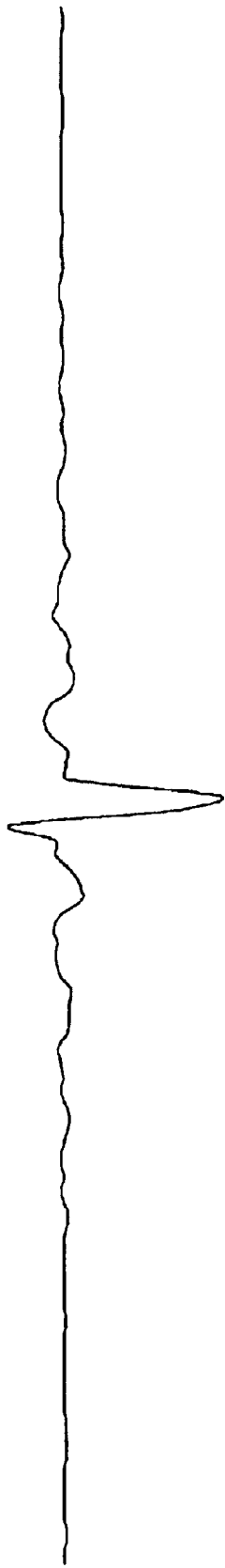
FIG. 13A illustrates the resultant signal of non-contaminated wavelet packet number 12 of FIG. 11.
Figure 13B:
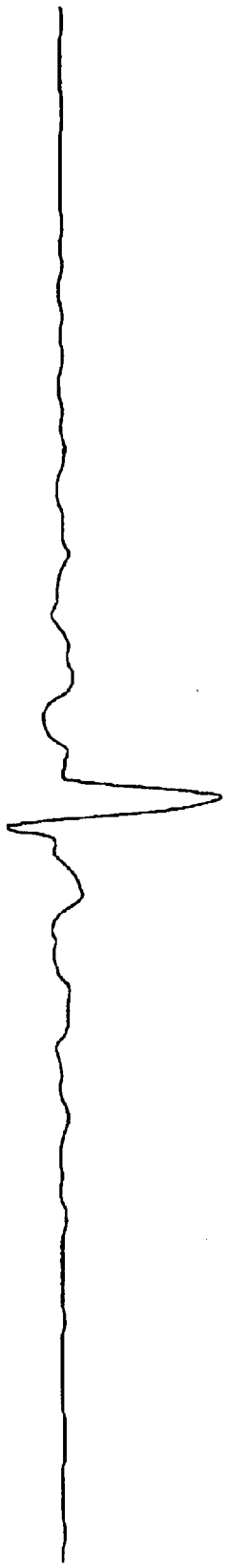
FIG. 13B illustrates the resultant signal of contaminated wavelet packet number 12 of FIG. 12.

Refer to FIGS. 11 and 12. For a particular example, it was determined that the mismatched wavelet-packets are wavelet-packet (WP) number 1 and WP number 12. Comparing FIGS. 11 and 12, WP 1 and 12 are mismatched since in FIG. 11 WP 1 does not branch and in FIG. 12 it does branch. The same is true of WP 12. All other shown WPs "match" in FIGS. 11 and 12, e.g., WP 2 branches in both, WP 5 branches in both, WP 6 does not branch in both, WP 11 branches in both. Note that not all branches shown in FIG. 12 are shown in FIG. 11. Therefore, the pair of WP 1s from each of FIGS. 11 and 12 constitute one mismatched pair and the pair of WP 12s from each of FIGS. 11 and 12 constitute a second mismatched pair, the only two mismatched pairs for the "best trees" shown in FIGS. 11 and 12. By using only mismatched pairs, the data are significantly reduced, facilitating more efficient computation. The lone interferogram signal of WP 12 (the best tree of a non-contaminated sample) is represented in FIG. 13A while its counterpart for the contaminated MUT is depicted in FIG. 13B, indicating how difficult it is to detect a contaminant visually without using the present invention.

A comparison of Q-values associated with the MUT (contaminated sample) 1401 to those with the pure (uncontaminated) known sample 1402 is provided in FIG. 14, together with the relative position of each as related to the constant Q-limit value 1403. It is obvious by comparing the information available from FIGS. 13A, B with the information available in FIG. 14, that the present invention provides a positive indication of the presence of even minute amounts of contaminants not otherwise readily available from a single process. It also provides this information without the need for redundant instrumentation and data taking as well as eliminating any possible need for redundant data processing from a single set of data.

Although specific procedures, steps and applications are discussed, other similar procedures, steps and applications, including those that may have only some of the steps used in the above described examples, may be suitable for determining the presence of small amounts of material in a compound and fall within the ambit of a preferred embodiment of the present invention as provided in the claims herein.

We claim:

1. A fast and efficient method for detecting, identifying, and localizing particular elements in a sample of material of unknown composition, from which a first data set is collected, by comparing said first data set to at least one second data set collected from at least one sample of said material of known composition, each said data set suitable for characterizing components of all said samples at least spectrally and spatially, comprising:

decomposing said first and second data sets by applying a pre-specified wavelet family to each said first and second data sets;

generating corresponding wavelet-packets (WPs) for each said decomposed data set using an entropy criterion;

generating a best tree for each WP, said best tree having nodes;

generating a branching/non-branching operation for each said best tree, wherein said branching/non-branching operation establishes a basis for comparing said nodes of said best trees of said first data set to corresponding said nodes of said best trees of said at least one second data set;

comparing said corresponding nodes from said branching/non-branching operation to identify for further processing only mismatched pairs of said nodes, wherein a mismatched pair comprises said corresponding node branching in one said best tree and said corresponding node not branching in another said best tree being compared;

employing a principal component analysis (PCA) for each said mismatched pair thus identified, placing in a first data file said data from said first data set corresponding to said corresponding nodes taken from one at least one second data set, but preferably from multiple said at least one second data sets;

generating a covariance matrix for said first data file;

deriving eigenvectors, eigenvalues and explained vectors from said covariance matrix;

adding only data associated with said corresponding node from said first data set to said first data file to obtain a second data file from which eigenvectors, eigenvalues and explained vectors are derived, calculating a Q-Limit to compare said first and second data files to a pre-specified threshold;

finding residuals of said second data file;

using said residuals, computing corresponding Q-Values, such that if said corresponding Q-values are higher than said calculated Q-Limit, the existence and location of components different from those components in said known composition is indicated as being in said material of unknown composition.

2. The method of claim 1 in which said entropy criterion is the Shannon Entropy criterion.

3. The method of claim 1 in which said entropy criterion is selected from the group consisting of: the Shannon Entropy criterion, the Threshold Entropy criterion, the Sure Entropy criterion, and any combination thereof.

4. A method for detecting, identifying, and localizing particular elements in a sample of material from which a first data set is collected involving comparing said first data set to at least one second data set collected from at least one sample of said material known not to contain measurable amounts of said particular elements, each said data set suitable for characterizing components of said samples at least spectrally and spatially, comprising:

decomposing said first data set;

decomposing said at least one second data set, wherein said decomposing of said first and second data sets is accomplished by applying to each said data sets at least one pre-specified wavelet family;

generating corresponding wavelet-packets for each said decomposed first and second data sets using an entropy criterion;

generating a best tree having nodes each representing one said corresponding wavelet packets for each said decomposed first and second data sets;

generating a branching/non-branching operation on each said best trees to establish a basis for comparison of nodes of said best trees, wherein said branching/non-branching operation is performed at each said node, and wherein an individual said node is used to form each said best tree if branching appears at one said node in a first said best tree and not at the other said equivalent node in a second said best tree, and wherein only said nodes present in both said first and second best trees are used in subsequent analysis;

employing a principal component analysis, for each said mismatched pair:

placing said data from said second data set corresponding to a same said node, but taken from a different sample, in a first data file;

generating a covariance matrix such that the data points of a first interferogram represent a first subset and that of a second interferogram represent a second subset, wherein elements of said covariance matrix are the variance of said first subset, the covariance of said first subset, the variance of said second subset, and the covariance of said second subset, and wherein first values of said interferograms are values of a first observation and $n^{th}$ values of said interferograms are values of an $n^{th}$ observation;

generating eigenvectors, eigenvalues, and explained vectors, wherein said generated eigenvectors, eigenvalues, and explained vectors characterize said covariance matrix;

employing said eigenvectors, eigenvalues and explained vectors, generating a Q-Limit, wherein all said eigenvalues are added, and wherein elements of said explained vector are used to establish a value on the impact of a particular measurement on the observed data as a whole, and wherein sums of said eigenvalues, squares of said eigenvalues, cubes of said eigenvalues together with a variance parameter that is normally distributed with zero mean and unit value are used to generate said Q-limit, and wherein said Q-limit is used for comparison of said first and second data files to a pre-specified threshold;

adding said data associated with a same node from said first data set to said first data file to obtain a second data file;

finding principal components of said second data file, wherein said principal components are generated using said eigenvectors of said covariance matrix, said interferograms and corresponding mean values of said interferograms; and using said principal components, computing corresponding Q-Values, wherein said Q-values are generated from the sums of the squares of said corresponding principal components, and wherein said corresponding Q-values higher than said calculated Q-Limit indicate existence of said particular matter in said tested sample of material at each location at which said particular material is observed.

5. The method of claim 4 in which said entropy criterion is the Shannon Entropy criterion.

6. The method of claim 4 in which said entropy criterion is selected from the group consisting of: the Shannon Entropy criterion, the Threshold Entropy criterion, the Sure Entropy criterion, and any combination thereof.

* * * * *

UNITED STATES PATENT AND TRADEMARK OFFICE
CERTIFICATE OF CORRECTION

PATENT NO.   : 6,859,764 B2
DATED        : February 22, 2005
INVENTOR(S)  : Castellane, Raymond H., Ahmad, Falih H. and Durst, Bartley P.

It is certified that error appears in the above-identified patent and that said Letters Patent is hereby corrected as shown below:

Title page,
Item [74], *Attorney, Agent, or Firm*, change "Earl H. Bougiter" to
-- Earl H. Baugher, Jr. --

Column 7,
Line 34, change from "A preferred embodiment of the present Invention estab-" to
-- A preferred embodiment of the present invention estab- --

Column 10,
Line 24, change the un-italicized "I" that is the first letter in the line to an italicized
-- *I* --

Column 16,
Line 27, change the equation from $H(s) = \sqrt{2\log_{e[n\log_2(n)]}}$ to $H(s) = \sqrt{2\log_e[n\log_2(n)]}$ Line 44, change the number "603" to a bolded number -- 603 --

Signed and Sealed this

Seventeenth Day of May, 2005

JON W. DUDAS
*Director of the United States Patent and Trademark Office*